United States Patent [19]

Male et al.

[11] Patent Number: 5,292,524

[45] Date of Patent: Mar. 8, 1994

[54] BLOOD PLATELET LOADED WITH DIAGNOSTIC OR THERAPEUTIC-CONTAINING LIPOSOME OR RECONSTITUTED SENDAI VIRUS

[75] Inventors: Roxanne Male, Pasadena; Wilton E. Vannier, Sierra Madre, both of Calif.

[73] Assignee: California Institute of Technology, Pasadena, Calif.

[21] Appl. No.: 755,835

[22] Filed: Sep. 6, 1991

[51] Int. Cl.$^5$ ............... A61K 37/22; A61K 43/00; A61K 49/04; A61M 36/14
[52] U.S. Cl. ................... 424/1.17; 424/450; 424/4; 424/532
[58] Field of Search ............. 424/532, 450, 4, 1.1

[56] References Cited

U.S. PATENT DOCUMENTS

| | | | |
|---|---|---|---|
| 4,938,948 | 7/1990 | Ring et al. | 424/9 |
| 5,047,245 | 9/1991 | Bally et al. | 424/450 |
| 5,213,788 | 5/1993 | Ranney | 424/9 |

FOREIGN PATENT DOCUMENTS

| | | | |
|---|---|---|---|
| 0016347 | 10/1991 | PCT Int'l Appl. | 424/450 |
| 2240547 | 8/1991 | United Kingdom | 424/450 |

OTHER PUBLICATIONS

Male et al (1992) *Proc. Natl. Acad. Sci. 89*, pp. 9191-9195.
Male et al (1991) *Faseb 5*, A523.
Doerschuk et al (1989) *Thrombosis and Haemostasis 61*, pp. 392-396.

*Primary Examiner*—Douglas W. Robinson
*Assistant Examiner*—Jeffrey J. Sevigny
*Attorney, Agent, or Firm*—Poms, Smith, Lande & Rose

[57] ABSTRACT

The invention provides loaded platelets that include an absorbed loading vehicle having associated diagnostic or therapeutic agents. A method of loading platelets with diagnostic or therapeutic agents is provided. The method includes combining a loading vehicle having associated diagnostics or therapeutic agents with platelets at sufficient concentration and temperature to allow uptake of the loading vehicle by the platelets. Also provided is a method of targeting diagnostic or therapeutic agents to platelet localizing areas. The method includes the steps of: (a) combining a loading vehicle having associated diagnostic or therapeutic agents with platelets at sufficient concentration and temperature to allow uptake of the loading vehicle by the platelets; (b) isolating the platelets from excess loading vehicle; and (c) administering the isolated platelets to an animal in an effective concentration so as to promote targeting of the isolated platelets to platelet localizing areas. A method of imaging is also provided.

10 Claims, No Drawings

BLOOD PLATELET LOADED WITH DIAGNOSTIC OR THERAPEUTIC-CONTAINING LIPOSOME OR RECONSTITUTED SENDAI VIRUS

This work was supported in part by United States Army Research Office Grant DAAC-03-87-K-0044 and NIH Traineeship No. 5-T32-GMO7616-13. The Government may have rights in the invention.

BACKGROUND OF THE INVENTION

This invention relates to the introduction of diagnostic or therapeutic agents into platelets and more specifically to the use of platelets having associated diagnostic or therapeutic agents for in vivo imaging and targeting.

Platelets are small cells derived from precursor megakaryocytes which control blood clotting and aid in repair of blood vessels. Because of their biological functions, platelets localize to specific areas of diseases including sites of inflammation, infection, thrombosis and neoplastic tumors.

Removal of foreign materials from the blood may also be a major physiological role for platelets. Platelets are known to endocytose a variety of particles in vitro, Clawson, C. C., Am. J. Pathol. 70:449–464, 1973, which is incorporated herein by reference. Particles and solutes may be endocytosed by different mechanisms, Zucker-Franklin, D. J., Cell Biol. 91:706–715, 1981, which is incorporated herein by reference. For example, uptake of particles is energy dependent and arrested when both oxidative phosphorylation and glycolysis are inhibited. Particle uptake is also divalent cation dependent and the process is usually associated with release of platelet granule contents into the extracellular media. On the other hand, the uptake of soluble substances is not energy dependent, is arrested at 4° C. and does not result in degranulation.

Previously, latex spheres have been used as a model for foreign particle ingestion by platelets. Progressive accumulation of latex spheres in the open channel system (OCS), a system of channels believed to be formed by invagination of the plasma membrane, was followed by localization of the particles in acid phosphatase-positive electron-opaque vacuoles, Lewis et al., Blood 47:833–840, 1976, which is incorporated herein by reference. Platelets have also been shown to take up virus particles. Influenza virus, a myxovirus, is taken up by platelets via the OCS, Jerushalmy et al., Proc. Soc. Exp. Biol. Med. 106:462–466, 1962, which is incorporated herein by reference. The mechanism of incorporation and the fate of the virus have not been determined.

Cellular uptake mechanisms such as phagocytosis and viral mediated uptake have been used for introducing drugs and macromolecules in vitro into specific cell types. Such drugs and macromolecules include inorganic and organic compounds, liposomes, red blood cell ghosts and polypeptides. For example, phagocytosis has been used to introduce liposome encapsulated muramyl dipeptide (MDP) into macrophages, Fidler et al., Cancer Res. 49:4665–4670 (1989), which is incorporated herein by reference. Monocytes have also been shown to ingest similar materials in vitro. Viral mediated mechanisms include uptake of Sendai virus, a murine paramyxovirus, which is capable of entering a cell through membrane fusion.

Although the applications are limited, preferential delivery of drugs and macromolecules to specific cell types in vivo has ben accomplished through nonspecific mechanisms such as phagocytosis. For example, liposomes loaded with agents which activate macrophages and thereby kill tumor cells have been used parenterally to treat tumor metastases. Macrophages are localized to various tissues and organs especially those of the reticuloendothelium system (e.g., liver, spleen, lymph nodes and lungs) and after phagocytosis of liposomes containing activating agents show increased rates of phagocytosis and killing of various infectious agents and tumor cells.

The applications described above cannot be employed for the specific targeting of drugs and macromolecules to many desired locations within an organism. Instead, such applications are limited to specific phagocytotic cell types and have been used to enhance a particular function exhibited by cells, such as enhanced tumoricidal rate of macrophages.

In vivo liposome delivery to macrophages and monocytes is also very inefficient. The percentage of liposomes taken up by these cells is small and therefore requires administration of liposomes in a large excess to achieve an effective delivery. Phagocytosis of the liposomes by other cell types is one factor which can account for this low efficiency. Additionally, the lipid composition of the liposome is another factor which influences their uptake.

Systems which employ particles other than liposomes have been used for diagnostic purposes. Platelets have been labeled with radio-isotopes and used for in vivo imaging. These methods involve chemically linking the imaging reagent to the platelet surface and can result in transfer of the label to other cells within the blood stream after injection. Such label transfer has unnecessary deleterious effects on the receiving cells, results in a lower effective amount to the imaged area and can also affect the resolution of the final image.

There exists a need to be able to target a variety of specific disease locations within an organism, organ or graft with effective amounts of diagnostic and therapeutic agents. The present invention satisfies this need and provides related advantages as well.

SUMMARY OF THE INVENTION

The invention provides loaded platelets that include an absorbed loading vehicle having associated diagnostic or therapeutic agents. A method of loading platelets with diagnostic or therapeutic agents is provided. The method includes combining a loading vehicle having associated diagnostics or therapeutic agents with platelets at sufficient concentration and temperature to allow uptake of the loading vehicle by the platelets. Also provided is a method of targeting diagnostic or therapeutic agents to platelet localizing areas. The method includes the steps of: (a) combining a loading vehicle having associated diagnostic or therapeutic agents with platelets at sufficient concentration and temperature to allow uptake of the loading vehicle by the platelets; (b) isolating the platelets from excess loading vehicle; and (c) administering the isolated platelets to an animal in an effective concentration so as to promote targeting of the isolated platelets to platelet localizing areas. A method of imaging is also provided.

DETAILED DESCRIPTION OF THE INVENTION

The invention is directed to methods for loading platelets and for targeting diagnostic or therapeutic agents to platelet localizing areas. In one embodiment, platelets are loaded with diagnostic or therapeutic agents by phagocytosis of liposomes containing such agents within their aqueous components. Uptake of liposomes occurs through the open channel system (OCS) and is followed by a moderate rate of exocytosis of the liposome's aqueous components.

In a second embodiment, platelets are loaded by receptor-mediated endocytosis. Various proteins can be coupled to the liposomes' surfaces that will induce such receptor-mediated endocytosis with platelets. Uptake of these protein coupled liposomes results in the uptake and retention of the liposomes' lipid and aqueous components within the cells.

In a third embodiment, platelets are loaded using reconstituted Sendai virus envelopes (RSVE). RSVEs can be prepared which contain diagnostic or therapeutic agents within their aqueous components and are able to mediate fusion comparable to intact Sendai virus. Once fusion is complete, the diagnostic or therapeutic agent is contained within the platelet's cytoplasm.

Loaded platelets can be used to diagnose or treat a variety of platelet associated conditions such as inflammation, metastases, thrombus and the like. A unique advantage of platelets is that they exhibit both circulatory and targeting functions and, therefore, can be loaded in vitro and subsequently administered to a patient's circulatory system for in vivo targeting of diagnostic or therapeutic agents.

As used herein, the term "loading" refers to the incorporation of material inside platelet. The incorporated material can be located, for example, within the cytoplasm of the platelet or be compartmentalized within a vacuole or organelle. The term "loading vehicle" as used herein, therefore refers to a particle which can be used to introduce such material into a platelet. A loading vehicle can be, for example, liposome vesicles such as neutral unilamellar liposomes, multilamellar liposomes or reconstituted Sendai virus envelopes. Lipid emulsions can also be used as loading vehicles. Lipid emulsions have the added advantage of being easier to prepare. Such loading vehicles can be produced such that water soluble or lipophilic diagnostic or therapeutic agents are contained within an interior compartment or associated with the lipid component of the loading vehicle. Modifications to the loading vehicle's surface can also be made. Such modifications can include, for example, placing specific ligands recognized by receptors on the platelet's surface or antibodies to platelet surface antigens.

As used herein, the term "uptake" refers to a biological process by which platelets absorb loading vehicles. The process can be, for example, phagocytosis, membrane fusion or receptor-mediated endocytosis. The pathway by which loading vehicles are taken up is not critical so long as the material to be incorporated inside a platelet successfully crosses the platelet cell membrane.

As used herein, the term "platelet localizing areas" refers to regions within a tissue, organ, graft or animal in which a platelet-mediated event takes place. Platelets are attracted to or can become attracted to such regions. Platelet localizing areas include, for example, any area where the protein clathrin is exposed. Thus, areas of inflammation, clots, lesions, thrombosis, metastasis and grafts are included within the definition.

A method of loading platelets with diagnostic or therapeutic agents is provided. The method includes combining loading vehicles having associated diagnostic or therapeutic agents with platelets at sufficient concentration and temperature to allow uptake of the loading vehicle by the platelets. Loaded platelets that include an absorbed loading vehicle having associated diagnostic or therapeutic agents are also provided.

Loading vehicles having associated diagnostic or therapeutic agents can be generated by methods well known in the art. For example, liposomes can be produced containing water soluble diagnostic or therapeutic agents within their aqueous components by reconstitution of lipids in the presence of the water soluble agent to form vesicles. This method entails solubilizing lipids in an organic solvent, evaporating off the solvent and adding an aqueous solution containing the diagnostic or therapeutic agent to the lipid. The mixture is subsequently sonicated to allow self-assembly to form the lipid vesicles which results in the trapping of aqueous components and its solutes within the liposome vesicle. Other methods include solubilizing the lipids in non-ionic detergents followed by slow dialysis against an aqueous buffer containing the diagnostic or therapeutic agent. Lipid analogs or hydrophobic derivatives of diagnostic or therapeutic agents can also be incorporated into the lipid bilayer by addition of the lipid analog to the lipids prior to evaporation of the organic solvent. In a similar fashion, the diagnostic or therapeutic agent can be attached, for example, by a covalent bond, to the lipids and then incorporated into the bilayer of the loading vehicles as described above. Analogous methodology is used to generate RSVEs containing soluble drug or therapeutic agents within its aqueous compartment.

Therapeutic agents to be incorporated into loading vehicles are those which provide beneficial results when used to treat platelet associated conditions. Diagnostic agents to be incorporated into loading vehicles are those which are able to detect platelet associated conditions. Platelet associated conditions are those associated with the biological functions of platelets. Platelets circulate in the blood stream and localize to injured or abnormal conditions. A specific example of such targeting is when platelets localize to a site of injury. Other conditions where the localizing of platelets occurs include, for example, thrombus formation, inflammation, infection, tissue grafts and to areas with neoplastic tumor cells. Therapeutic agents for treating such conditions can therefore include, for example, activating agents or platelet activating factors. Such agents and factors include, for example, bacterial products, cell wall materials or synthetic analogs such as Murimyl dipeptide. Other therapeutic agents for treating platelet associated conditions include, for example, adriamycin, cis-platinum (cis-Pt), anti-tumor reagents, or thrombolytic reagents such as TPA and photosensitizers for killing tumor cells. A variety of other therapeutic agents are known within the art for the treatment of platelet associated conditions. They range from inorganic to organic compounds to larger macromolecules and can also be incorporated into the loading vehicles described herein by one skilled in the art.

Diagnostic agents for detecting platelet associated conditions can be used by themselves or in conjunction with therapeutic agents to simultaneously diagnose and treat a platelet associated conditions. Such agents can be, for example, macromolecules labeled with a radioisotope such as gamma-emitters, positron-emitters and x-ray-emitters. Labels include, for example, indium-111, technetium-99m, iodine-125, gallium-67 and gallium-68.

Other agents known by one skilled in the art can be used as well.

Uptake of loading vehicles initially occurs via diffusion into the OCS, followed by a phagocytotic process into the platelet. The liposomes are taken up intact, subsequently disrupted and the aqueous components are then exocytosed at a moderate rate. Disruption of liposomes most likely occurs in electron-opaque vacuoles which contain acid phosphatase, Lewis et al., Blood 47:833–840, 1976, which is incorporated herein by reference. Release of aqueous components to the external space probably involves the migration of these vacuoles to the periphery of the cell and exocytosis of their contents.

Although the space available for uptake within the cell is limited, the exocytosis of the aqueous components of the liposomes increases the amount of liposome lipid or lipid associated agents capable of being stored. On the time scale of the competition experiments shown in Example I, up to about six hours, the space available for uptake is not saturable. Uptake is independent of the amount of competitor liposomes added and their preincubation times. However, competition experiments performed without preincubation of competitor liposomes, i.e., simultaneous incubation, demonstrated a dilution effect.

The values reported herein, which characterize platelet uptake using labeled liposomes, do not differentiate between incorporated and surface-bound liposomes. However, electron micrographs (EM) indicate that the vast majority of the liposomes are encapsulated within the platelet. Additionally, studies using pyranine, a pH-dependent fluorescent liposome probe, confirmed the EM observations showing that liposomes are phagocytosed and are ultimately contained in acid-containing compartments. These results suggest that liposomes are taken up in surface invaginations which pinch off their connections to the cell wall and migrate into the cytoplasm as sealed vesicles, rather than being sequestered in the OCS and in contact with the outside media. Degradation of the liposomes, which probably occurs in the acid-containing vacuoles via esterases, has also been demonstrated by utilizing liposomes labeled with cholesteryl[$^{14}$C]oleate.

The process of platelet phagocytosis can be inhibited by a variety of agents. For example, addition of EDTA greatly diminishes phagocytic uptake of liposomes. Liposomes are able, however, to adhere to platelets in the presence of EDTA, indicating that divalent cations are involved in the phagocytosis process. Inhibitory effects of cytochalasin B on platelet uptake has previously been attributed to its effects on microfilaments and to the plasticity of the platelet membrane, White, J. G. and Krumweide, M., Blood 41:823–832, 1973, which is incorporated herein by reference. Cytochalasin B was able to inhibit platelet uptake, albeit with lower efficiency than that reported in the art. Inhibitors of oxidative phosphorylation and glycolysis such as 2,4-dinitrophenol and iodoacetate also inhibited platelet phagocytosis of liposomes. These studies are consistent with a phagocytic mechanism for platelet uptake of liposomes.

Examination of the fate of the phagocytosed liposome-derived aqueous components revealed an exocytotic process having a moderate rate. The half-life of the aqueous compartment calculated from $k_2$ is about 3.9 hours (see Example I under Kinetics of Liposome Uptake and Exocytosis). A half-life of this duration is sufficient in most cases to use platelets loaded by liposome phagocytosis for in vivo treatment of platelet associated conditions. If longer half-lives are needed, lipid analogues of diagnostic or therapeutic agents can be used, for example, to increase platelet retention of the diagnostic or therapeutic agent. Longer retention of lipid analogs is because the lipid component of a loading vehicle will remain with the platelet for a longer period of time and not be exocytosed as rapidly as the aqueous component. This observation is demonstrated in Example I by the retention of $^3$H-cholesteryl hexadecyl ether. Similarly, lipophilic diagnostic or therapeutic agents and agents attached to lipids will also be retained by the platelet longer. If decreased half-lives are desired for a particular application, then lipids which result in less stable liposomes can be used to achieve this purpose. Thus, the kinetics of exocytosis can be modulated varying the composition of the lipid component of loading vehicles. One skilled in the art will know or can determine using the teachings described herein which lipid components will achieve the desired need.

In addition, platelet uptake of liposomes with human gamma globulin (HgG) or transferrin covalently coupled to their surfaces has also been performed. The HgG coupled liposomes are taken up via Fc receptor mediated endocytosis. Uptake of these liposomes results in the retention of both the lipid and aqueous components. Unlike the uptake of control liposomes, uptake of HgG coupled liposomes is saturable. Preincubation with competitor HgG coupled liposomes results in decreased uptake. In addition, preincubation of the platelets with free HgG, which blocks the Fc receptor, inhibits uptake of HgG-coupled liposomes.

As described below, RSVE-type loading vehicles are also taken up and their aqueous contents retained by platelets. Uptake of RSVE by platelets proceeds through a similar mechanism to that of intact Sendai virus fusion with cell types other than platelets. Sendai virus fusion with cell membranes occurs via the function of two glycoproteins, the hemagglutinin/-neuraminidase (HN) protein which mediates binding of the virus particles to the cell surface receptors and the fusion (F) protein which is essential for promotion of virus-cell fusion, White J. M., Annu. Rev. Physiol. 675–695, 1990, which is incorporated herein by reference. The Sendai virus envelope components become part of the cell membrane and the virus contents are deposited into the cell's cytoplasm.

For loading macromolecules, Sendai viral envelopes are solubilized by incubation with non-ionic detergents. Detergent solubilized fractions contain, in part, the HN and F proteins and when soluble macromolecules are present, they are trapped within the membranes of subsequently formed vesicles after removal of detergent, White, J. M., 1990, supra. Fusion activity of such reconstituted virus envelopes is comparable to that of the intact virus, Hansen et al., Eur. J. Biochem. 149:591–599, 1985, which is incorporated herein by reference.

Initial characterization of the mechanism of platelet uptake was examined using labeled virus or RSVE. These experiments do not differentiate between fusion and phagocytosis and the results reported reflect all processes of uptake including surface binding. In contrast to liposomes, uptake of labeled virus particles is time dependent and shows saturation at longer incubation periods. Uptake is also dependent on the number of virus particles incubated and increases with increasing virus concentration. Saturation can be demonstrated at higher concentrations.

Uptake of RSVE is also temperature dependent. At 37° C., platelets take up approximately twice the amount as at 4° C. The majority of Sendai virus associated with the cells at 4° C. is probably bound to the platelets' surfaces since fusion and phagocytosis are negligible at this temperature. Uptake values for $^{125}$I-labeled RSVE exceed those for $^{125}$I-labeled Sendai virus. Although there is no clear explanation, this difference has been reported for Sendai virus and RSVE uptake with cells other than platelets.

Virus localization within the OCS indicated that platelet phagocytosis might be occurring. However, there was no measurable decrease in the pH as detected by pyranine, the pH-sensitive probe described above for liposome phagocytosis. Fate of the RSVE aqueous compartment and protein components was examined and both were found to be retained by the platelets. Moreover, preincubation of platelets with non-labeled competitor virus resulted in decreased uptake of labeled virus. Contrary to phagocytosis, fusion is receptor mediated; the receptors are composed of sialic acid containing molecules, and can be saturated as shown in Example II. Taken together, these results indicate that RSVEs are taken up by platelets via a fusion mechanism and that their aqueous contents are retained longer than those taken up by phagocytosis.

Fusion was also monitored using an $R_{18}$ fluorescence assay as described in Example II (see section entitled RSVE Fusion with Platelets). Fusion of Sendai virus particles with platelets was similar to those seen for other cells. Fusion is biphasic; initial uptake increases rapidly over a two minute period and then proceeds more slowly until saturation is reached. The percent fusion decreases with increasing amounts of incubated virus and increases with increasing amounts of platelets added. Fusion is maximal at 37° C. and pH=7.4. The percent fusion seen at 4° C. may represent residual fusion or fusion-independent transfer of the $R_{18}$ probe.

To further show that fusion is the predominant process, platelets and/or RSVE were incubated with chemicals known to inhibit fusion or phagocytosis. For example, gangliosides are known receptors for Sendai virus and are able to block reactive sites on the virus. Trypsinization of virus particles destroys the fusion protein which is essential for fusion. EDTA, on the other hand, chelates divalent cations which are essential for platelet phagocytosis. Cytochalasin B alters the plasticity of platelet membranes and decreases OCS uptake. The combination of 2,4 dinitrophenol/iodoacetate inhibits glycolysis and oxidative phosphorylation which is necessary for phagocytosis.

These chemicals were tested for their ability to inhibit RSVE uptake. Addition of gangliosides GD1$a$ and GT1$b$ to virus particles prior to incubation with platelets was able to inhibit uptake. Likewise, trypsinization of virus particles prior to incubation also decreased uptake. However, uptake was not inhibited by incubation in 1 mM EDTA, preincubation of the cells with cytochalasin B or the addition of 2,4 dinitrophenol and iodoacetate to the platelet solution. Taken together, these results indicate that the predominant interaction between platelets and Sendai virus particles is fusion.

An advantage of using reconstituted Sendai virus to load platelets is its ability to deliver aqueous substances to the cells without subsequent exocytosis as in the liposome loading vehicle system. Disadvantages of this system include leakage of encapsulated material, a decrease in fusion activity with increasing time of RSVE storage, and the decoration of the platelet membrane with viral proteins after fusion which might later modify the platelet's interactions in vivo. For example, significant rates of leakage for RSVE encapsulated carboxyfluorescein (molecular weight 376) have been detected as well as a complete loss in RSVE fusion activity after only a few days at −20° C. The decrease in fusion activity is more rapid at room temperature and is predominantly due to the decrease in fusion protein activity; the hemagglutinin/neuraminidase activity persists for several days.

A method of targeting diagnostic or therapeutic agents to platelet localizing areas is provided. The method includes: (a) combining loading vehicles having associated diagnostic or therapeutic agents with platelets at sufficient concentration and temperature to allow uptake of the loading vehicles by the platelets; (b) isolating platelets from excess loading vehicle; and (c) administering the isolated platelets to an animal in an effective concentration so as to promote targeting of the isolated platelets to platelet localizing areas.

A method of imaging platelet associated conditions is also provided. The method includes: (a) combining loading vehicles having associated diagnostic agents with platelets at sufficient concentration and temperature to allow uptake of the loading vehicles by the platelets; (b) isolating the platelets from excess loading vehicle; (c) administering the isolated platelets to an animal in an effective concentration so as to promote targeting of the isolated platelets to platelet localizing areas; and (d) detecting the diagnostic agent.

Platelets loaded by the methods described herein can be used as a delivery system for diagnostic or therapeutic agents to platelet localizing regions within an animal. For example, a variety of diagnostic or therapeutic agents can be encapsulated into platelets in vitro using the loading vehicles and methods described above. The diagnostic or therapeutic agents which are specific for a particular application would be chosen. For example, drugs, macrophage activators or other biologic response modifiers such as interleukins or cytokines can be targeted to areas of inflammation or infection or used for more general stimulation of the immune response. Targeting to regions of tumor cell metastases can allow stimulation and activation of NK cells or cytotoxic lymphocytes associated with the tumor metastases for tumor cell killing. Diagnosing areas of platelet accumulation such as a thrombus would require a labeled macromolecule or liposome which could be detected by imaging. The diagnostic or therapeutic agent which should be chosen for a desired diagnostic or targeting application will be known by one skilled in the art. Loaded platelets can be loaded and used immediately for in vivo targeting or loaded and stored for later use. Storage of loaded platelets is preferably done at room temperature or at cryogenic temperatures.

Once the platelets have been loaded, in vivo targeting of the diagnostic or therapeutic agent to specific location is accomplished by administering the loaded platelets to an animal subject. The animal subject can be a human. Administration can be performed, for example, by intravenous injection or intraperitoneal injection into the animal's circulatory system. A sufficient number of loaded platelets should be used to allow the localization of an effective amount of loaded platelets to targeted regions. Alternatively, if a transplant is to be performed, loaded platelets can first be administered to the organ or tissue or graft thereof to target injured regions prior to transplanting.

Targeting is accomplished via the biological functions of the platelets themselves. Adhesion molecules on the platelet surface specifically interact with receptors at injured tissues or abnormal cells. A specific example of such receptors which interact with platelet adhesion molecules is clatharin. This receptor molecule is normally found cytoplasmically associated with coated pits but is exposed to the extracellular space if the tissue is injured. Thus, platelets containing diagnostic or therapeutic agents beneficial to the recovery of platelet associated conditions will inherently deliver their contents to such areas.

For diagnosing a platelet associated condition, the sites of platelet localization can be determined after targeting by standard imaging techniques. Such techniques are known to one skilled in the art and include, for example, planar imaging, single photon emission computed tomography (SPECT) and gamma camera whole body imaging.

The following examples are intended to illustrate but not limit the invention.

EXAMPLE I $^3$H-cholesterylhexadecyl Ether Labeled Liposome Uptake

This section shows the uptake of $^3$H-cholesterylhexadecyl ether labeled liposomes by platelets for varying incubation times and liposome concentrations of both the liposomes and platelets.

For platelet purification, platelet-rich plasma packs obtained from the Red Cross were diluted in a 1:1 ratio with 0.9% saline solution. A volume of 4.5% dextran (molecular weight 250,000) in saline solution was added to an equal volume of the diluted packs and stirred; the red blood cells were allowed to sediment for 30 minutes at room temperature. Fifteen mL aliquots of the supernatant were pipetted into centrifuge tubes. Equal volumes of a solution containing 6.35% Ficoll and 10% Hypaque w/w were gently layered on the bottom of the tubes. The tubes were spun at 400 g for 15 minutes at room temperature. The cloudy band containing the platelets and lymphocytes located directly above the Ficoll-Hypaque gradient was gently removed, diluted in a 1:1 ratio with saline solution and centrifuged at 300 g for 15 minutes at room temperature to sediment the lymphocytes. The supernatant was spun at 800 g for 20 minutes; the platelet pellet formed was washed twice in saline solution and finally resuspended in Hanks' Balanced Salt Solution (HBSS). The final purity of the sample was greater than 95% platelets as assessed by a Colter S+4 Cell Counter; the main contaminants were red blood cells.

To determine the number of platelets per mg of protein, cell counts were first performed with a Colter S+4 Cell Counter to determine the number of platelets. The Peterson modification of the Lowry protein assay, Peterson, G. L., A Simplification of the Protein Assay of Lowry et al Which is More Generally Applicable, Anal. Biochem. 83:346-356, 1977, which is incorporated herein by reference, with a bovine serum albumin standard and without TCA precipitation was then used to determine the amount of protein in the same samples. A milligram of protein was found to correspond to $3 \times 10^8$ platelets.

$^3$H-cholesterylhexadecyl ether liposomes were prepared by mixing a 2:1 mole ratio of distearoylphosphatidylcholine (Avanti Polar-Lipids, Inc., Birmingham, Ala.) and cholesterol (cell culture tested Sigma Chemical Co., St. Louis, Mo.) in chloroform such that the total lipid content was approximately 20 mg. Five $\mu$Ci of $^3$H-cholesterylhexadecyl ether (New England Nuclear, Boston, Mass.) in chloroform was also added. The solution was then taken to dryness in a 100 ml round bottom flask with a Buchler "Rotovap" apparatus (Büchi, Switzerland). To ensure removal of all the chloroform, the sample was dried under vacuum overnight. The resulting phospholipid mixture was resuspended in 5 mL of PBS (0.90% NaCl: 0.12% Na$_2$HPO$_4$•7H$_2$O: 0.013% NaH$_2$PO$_4$•H$_2$O w/w in water, pH=7.3), vortexed and 2.5 ml portions probe sonicated for 15 minutes using a Heat Systems-Ultrasonics, Inc. (Farmingdale, N.Y.) sonicator with a microprobe.

Platelets and liposomes were incubated at 37° C. in 1.5 mL polypropylene centrifuge tubes for the desired incubation times after which the mixtures were centrifuged at 5700 g for 5 minutes in a Beckman Microfuge 11 (Beckman, Carlsbad, Calif.). The pellets were washed twice in saline solution and finally resuspended in 0.5 M NaOH/0.5% SDS and incubated overnight at room temperature. The solution was transferred to liquid scintillation vials with 10 mL of Safety Solve (Research Products, Inc., (Mount Prospect, Ill.), mixed and allowed to sit at least two hours prior to scintillation counting. For each experiment all samples were done in duplicate and all experiments were carried out at least twice.

The liposome diameters for different preparations were determined by photon correlation spectroscopy at 480 nm using a Malvern Instruments PCS 100 system (Malvern, England) The numbers of $^3$H-cholesterylhexadecyl ether labeled liposomes were calculated by assuming that the counts per weight of lipid were constant for all preparations, the average surface area for a phospholipid molecule is 0.7 nm$^2$, Rand, R. P, and V. A. Parsegian, Hydration Forces Between Phospholipid Bilayers, Bichim. Biophys. Acta 988:351-376, 1989, which is incorporated herein by reference, and the average molecular weight for the lipid is 656 g/mole. The numbers of $^3$H-inulin labeled and non-radiolabeled liposomes were determined by performing Böttcher phosphate assays Böttcher, F. J. F., et al., A Rapid and Sensitive Sub-micron Phosphorus Determination, Analytical Chimica Acta 24:203-204, 1961, which is incorporated herein by reference, on the samples and assuming a 0.7 nm$^2$ phospholipid surface area. The light scattering data indicated that the liposomes diameters were 65 to 83 nm. The number of liposomes reported have all been normalized assuming that the diameters of the liposomes for all experiments were 74 nm.

Platelet uptake of $^3$H-cholesterylhexadecyl ether labeled liposomes increased linearly with increasing incubation times Table 1. After incubation of $3 \times 10^8$ platelets with $7 \times 10^{11}$ liposomes for 24 hours, approximately 500 liposomes were associated with each platelet. Liposome uptake by platelets also increased linearly with increasing numbers of incubated liposomes; two incubation times are shown in Table 2. Incubation for 18.5 hours resulted in greater uptake values than the 12.5 hour incubation. As the number of platelets incubated with a set amount of liposomes was increased the overall number of liposomes incorporated increased Table 3; however the ratio of liposomes to platelets remained constant at approximately 450 liposomes/platelet for a 12.0 hour incubation period.

TABLE 1

| Time, hours | 0.5 | 1.0 | 2.0 | 3.0 | 4.0 | 5.0 | 6.0 | 7.0 | 8.0 | 9.0 | 10.0 |
|---|---|---|---|---|---|---|---|---|---|---|---|
| #Lip. per Platelet | 132 | 177 | 211 | 223 | 255 | 295 | 274 | 274 | 301 | 319 | 317 |
| Time, hours | 11.0 | 12.0 | 14.0 | 15.0 | 16.0 | 17.0 | 19.0 | 20.0 | 21.0 | 23.0 | 24.0 |
| #Lip. per Platelet | 360 | 380 | 433 | 474 | 469 | 523 | 490 | 480 | 513 | 519 | 533 |

TABLE 2

| Lip. $\times 10^{11}$ Added | 14.0 | 21.0 | 28.0 | 63.0 | 84.0 | 168.0 | 336.0 |
|---|---|---|---|---|---|---|---|
| #Lip. per Platelet (18.5 hr.) | 593 | 656 | 734 | 831 | 840 | 2082 | 4740 |
| #Lip. per Platelet (12.5 hr.) | 532 | 642 | — | 703 | 769 | 1271 | 1474 |

TABLE 3

| Platelets $\times 10^8$ Added | 0.6 | 1.2 | 3.0 | 3.6 | 4.2 | 4.8 | 5.4 | 6.0 |
|---|---|---|---|---|---|---|---|---|
| #Liposomes $\times 10^{10}$ | | 3.2 | 4.9 | 15.2 | 21.3 | 19.8 | 15.7 | 23.5 | 23.0 |

$^3$H-inulin Labeled Liposome Uptake

This section shows uptake of aqueous components of the liposomes by following the uptake of $^3$H-inulin labeled liposomes versus varying incubation times and liposome concentrations.

$^3$H-inulin labeled liposomes were prepared exactly as described in above except that no $^3$H-cholesterylhexadecyl ether was added and the resuspension buffer contained 5 μCi of $^3$H-inulin (Amersham, Corp., Arlington Heights, Ill.). Excess $^3$H-inulin was separated from the liposomes by gel filtration with a Sephadex G-50-100 column.

Although the number of $^3$H-inulin labeled liposomes endocytosed increased with time Table 4, the kinetics of uptake was different than that for the $^3$H-cholesterylhexadecyl ether labeled liposomes. Incubation of $2 \times 10^{12}$ liposomes with $3 \times 10^8$ platelets resulted in the uptake of approximately 275 liposomes per platelet after 24 hours. The uptake of $^3$H-inulin labeled liposomes versus the concentration of liposomes incubated is shown for two different incubation times Table 5. Uptake was proportional to both the amount of liposomes incubated and the incubation time.

TABLE 4

| Time, hours | 1.0 | 2.0 | 4.0 | 6.0 | 8.0 | 11.0 | 13.0 | 15.0 | 16.0 | 17.0 | 18.0 | 20.0 | 22.0 | 24.0 |
|---|---|---|---|---|---|---|---|---|---|---|---|---|---|---|
| #Lip. per Platelet | 166 | 158 | 155 | 181 | 162 | 231 | 180 | 223 | 210 | 266 | 173 | 181 | 241 | 218 |

TABLE 5

| #Liposomes $\times 10^{11}$ Added | 8.3 | 16.6 | 33.2 | 66.4 | 132.8 |
|---|---|---|---|---|---|
| Liposomes per Platelet (12.5 hours) | 27 | 44 | 50 | 78 | 132 |
| Liposomes per Platelet (6.0 hours) | 29 | 38 | 64 | 62 | 100 |

Release of the Tritiated Radiolabels

This section shows the exocytosis of liposome aqueous components following platelet uptake.

Platelets and liposomes were incubated as above for 12 hours. The mixtures were centrifuged and the platelets washed by centrifugation twice in HBSS and further incubated at 37° C. for varying periods of time. Both the pellets and supernatants were collected by centrifugation, solubilized in the NaOH/SDS solution overnight and counted.

The amount of tritiated radiolabels released, $^3$H-cholesterylhexadecyl ether and $^3$H-inulin probes are shown in Table 6. After 12 hours no membrane associated probe is released. However, up to 60% of the aqueous phase probe was released during this period.

TABLE 6

| Time, hours | 0.0 | 1.0 | 2.0 | 3.0 | 4.0 | 5.0 | 6.0 | 7.0 | 8.0 | 9.0 | 10.0 |
|---|---|---|---|---|---|---|---|---|---|---|---|
| $^3$H-Lipid | 0.0 | 5.2 | 7.7 | 8.1 | 2.8 | 8.7 | 5.4 | 3.4 | 5.4 | 5.5 | 2.7 |
| $^3$H-Aqueous | 0.0 | 14.1 | 33.6 | 43.5 | 28.2 | 51.1 | 65.5 | 57.5 | 47.6 | 46.0 | 57.2 |

HPTS Labeled Liposome Uptake

This section quantitates the percent of liposomes endocytosed and delivered to acidic compartments.

Pyranine (1-hydroxypyrene-3,6,8-trisulfonic acid, HPTS) liposomes were prepared as described above except that the resuspension solution was 35 mM HPTS (Molecular Probes, Eugene, Oregon) and 75 mM NaCl. Excess HPTS was removed by gel filtration with a Sephadex G-50-100 column equilibrated with 150 mM NaCl.

After incubation with HPTS labeled liposomes for various times, the cells were washed twice with HBSS. Fluorescence excitation spectra (lamda$_{ex}$ 395–465 nm, 4 nm bandwidth) were measured at 510 nm emission (4 nm bandwidth) using a SLM 4800 (SLM Instruments, Inc.) outfitted with a stirred, temperature controlled cuvette (20° C.). HPTS is a pH-dependent dye which exhibits two major fluorescence maxima (403 and 460 nm) which have a complementary pH dependence in the range 5–9; the peak at 403 nm is maximal at low pH values while the peak at 460 nm is maximal at high pH values. The fluorescence at 413 nm is relatively pH-independent and is used to standardize the concentration of dye associated with the cells. The fraction of dye taken up by endocytosis and delivered to an acidic, pH=6.0, environment was calculated using the 460/413 nm ratio and the equation:

$$\text{Fraction endocytosed} = (\text{ratio}_{pH\ 7.4} - \text{ratio}_{measured})/(\text{ratio}_{pH\ 7.4} - \text{ratio}_{pH\ 6.0})$$

where ratio$_{measured}$ is the 460/413 ratio of the liposome treated cells and ratio$_{pH\ 7.4}$ and ratio$_{pH\ 6.0}$ are the 460/413 ratios of liposomes in HBSS and acidified HBSS respectively, Daleke et al., Biochim. Biophys. Acta. 1024:352–366, 1990, which is incorporated herein by reference. In the original paper by Daleke et al., the second peak occurred at 450 nm; however, according to our data the peak maximum is at 460 nm.

The uptake of fluorescently labeled (HPTS) liposomes was measured by fluorimetry versus time (Table 7). Initially the liposomes were associated with the platelets, either bound to the surface or contained in the OCS, but were not endocytosed. Within minutes the liposomes began to accumulate in acid-containing vesicles. The percent of the platelet associated liposomes endocytosed increased to 80% within one hour.

TABLE 7

| Time, minutes | 5.0 | 10.0 | 15.0 | 20.0 | 25.0 | 30.0 | 35.0 | 40.0 | 45.0 | 50.0 | 55.0 | 60.0 |
|---|---|---|---|---|---|---|---|---|---|---|---|---|
| Percent Endocytosed | 0.0 | 0.0 | 11.2 | 19.1 | 20.1 | 31.7 | 23.7 | 43.4 | 48.6 | 56.3 | 54.3 | 86.7 |

TABLE 8

| Time, minutes | 10 | 20 | 30 | 40 | 50 | 60 |
|---|---|---|---|---|---|---|
| $^3$H/$^{14}$C within the Platelets | 1.02 | 1.10 | 1.19 | 1.08 | 1.20 | 1.33 |

Localization of Liposomes During Phagocytosis

This section shows the localization of liposomes within the platelet OCS.

Electron microscopy was performed to investigate the location of the liposomes with respect to the platelets. Samples of $3 \times 10^8$ platelets were $7 \times 10^{11}$ non-radiolabeled liposomes (prepared as described in Example I but without the tritiated labels) for 6 hours at 37° C. and then washed twice in saline solution. The samples were incubated in 1% glutaraldehyde in 0.1 M cacodylate buffer (pH=7.4) for 15 minutes and then centrifuged at 800 g. Postfixing in 2% osmium tetroxide was done in the dark at 4° C. for 0.5 to 2 hours followed by centrifugation at 800 g and washing in the buffer. Dehydration Cholesteryl[$^{14}$C]oleate Labeled Liposome Degradation This section shows the intralysosomal degradation of liposomes following platelet uptake.

Cholesteryl[$^{14}$C]oleate labeled liposomes were prepared as described above for the $^3$H-cholesterylhexadecyl ether labeled liposomes except 5 μCi cholesteryl[$^{14}$C]oleate (Amersham, Corp.) in chloroform was added during reconstitution.

Liposome degradation was monitored by studying the time dependence of the relative abundances of $^3$H and $^{14}$C within the platelets after preincubating the cells with $^3$H-cholesterylhexadecyl ether or cholesteryl[$^{14}$C]oleate labeled liposomes for half an hour.

Briefly, platelets were preincubated with identical amounts of $^3$H-cholesterylhexadecyl ether or cholesteryl[$^{14}$C]oleate labeled liposomes for half an hour at 37° C. The mixtures were washed twice in HBSS by centrifugation. The pellets were collected, resuspended in HBSS and incubated for 10 to 50 minutes at 37° C. Following incubation, the mixtures were centrifuged to collect the pellets that were then solubilized in NaOH/SDS solution overnight and counted.

Upon intralysosoma degradation cholesteryl[$^{14}$C]oleate is hydrolysed to form [$^{14}$C]oleate which is rapidly released from cells. Conversely, $^3$H-cholesterylhexadecyl ether is retained within the cell. Therefore, by monitoring the $^3$H/$^{14}$C ratio of the pellets, the degree of intralysosomal degradation can be determined, Derksen et al., Biochim. Biophys. Acts. 971:127–136 1988, which is incorporated herein by reference.

During a sixty minute time period, the $^3$H/$^{14}$C ratios within the cells increased (Table 8). $^3$H-cholesterylhexadecyl ether was retained within the platelets; however the cholesteryl[$^{14}$C]oleate was hydrolysed to form [$^{14}$C]oleate which was rapidly released by the cells. Therefore the increase in the $^3$H/$^{14}$C ratio in the cells was indicative of intralysosomal degradation of the liposomes.

was accomplished by immersing the sample in a series of solutions 50% through 100% ethanol for 5 minutes each. At this point the sample was transferred to a gelatin capsule and centrifuged. LR white, the embedding agent, was added and crosslinked and dried at 4° C. for 2–3 days under an ultraviolet lamp. Sliced sections were stained with 2% uranyl acetate for 5 minutes, then rinsed 50 times and blotted dry. An 8 mM solution of acidic lead citrate was then added and rinsed thoroughly.

Electron micrographs showed liposomes within the OCS with very few bound to the platelet surface. Because the liposomes are not very electron dense, visualizing the liposomes in the electron-opaque vacuoles by electron microscopy was not possible. An attempt was made to encapsulate 5 nm gold particles in the liposomes to facilitate visualization of the liposomes within the cells. However, poor encapsulation and platelet phagocytosis of residual free gold negated the usefulness of this technique.

Saturability and Inhibition of Liposome Uptake

This section shows that liposome uptake is non-saturable. It also shows that chemicals known to inhibit uptake of latex spheres also inhibited uptake of lysosomes.

A competitive assay was performed to establish whether liposome uptake could be saturated. Preincubation of platelets with non-radiolabeled liposomes prior to incubation with tritiated liposomes for preincubation times of 0.5, 2 and 6 hours and incubation times of 0.17, 0.5, 2 and 6 hours gave similar results. The amount of $^3$H-cholesterylhexadecyl ether liposomes taken up was independent of the amount of non-radiolabeled liposomes previously added. In addition, uptake was relatively independent of the preincubation time while uptake increased with increasing incubation times. Simultaneous incubation of non-radiolabeled and tritiated liposomes resulted in a linear decrease in uptake of the tritiated liposomes.

The inhibitory effects of a variety of chemicals known to decrease platelet uptake of latex spheres were examined during platelet incubation with liposomes. Incubation in the presence of 1 mM EDTA drastically inhibited the endocytosis of liposomes (Table 9). The addition of 10 μg/ml of cytochalasin B or $2.5 \times 10^{-4}$ M 2,4 dinitrophenol and $5 \times 10^{-5}$ M iodoacetate also inhibited uptake (Table 1).

TABLE 9

| #Lip. $\times 10^{10}$ Added | 7.0 | 14.0 | 21.0 | 28.0 | 35.0 | 42.0 | 49.0 | 56.0 | 63.0 | 70 |
|---|---|---|---|---|---|---|---|---|---|---|
| #Lip. per Platelet (2 hours, buffer) | 25 | 53 | 79 | 112 | 172 | 204 | 226 | 257 | 321 | 339 |
| #Lip. per Platelet (18.5 hours, buffer) | 37 | 78 | 118 | 161 | 260 | 297 | 350 | 405 | 458 | 475 |
| #Lip. per Platelet (2 hours, EDTA) | 5 | 6 | 7 | 10 | 9 | 9 | 14 | 15 | 13 | 20 |
| #Lip. per Platelet (18.5 hours, buffer) | 8 | 20 | 30 | 55 | 49 | 47 | 79 | 74 | 95 | 78 |

TABLE 10

| #Lip. $\times 10^{10}$ Added | 79 | 158 | 316 | 474 | 632 | 790 |
|---|---|---|---|---|---|---|
| #Lip. per Platelet (Buffer) | 110 | 241 | 338 | 712 | — | 1188 |
| #Lip. per Platelet (Cytochalasin B) | — | 79 | 170 | 399 | 560 | — |
| #Lip. per Platelet (Dinitrophenol/ Iodoacetate) | 70 | 83 | 170 | 209 | 269 | 325 |

Kinetics of Liposome Uptake and Exocytosis

Based on the uptake and exocytosis data of both of the $^3$H-labeled liposomes, the information gained by electron microscopy and studies with the cholesteryl[$^{14}$C]oleate and pH-sensitive fluorescent lipid probes, the following model was proposed for platelet interaction with liposomes. Initially the liposomes are probably reversibly associated with the platelets, either as bound particles or contained in the OCS. Within one o hour the majority of the liposomes are endocytosed into acid containing vesicles. Eventually the liposomes are degraded and the lipid components are sequestered within the cell and the aqueous components are exocytosed.

Using this model, the kinetics of uptake of the liposomes and exocytosis of the aqueous components were determined. For all uptake experiments the amounts of liposomes added were in excess; the amounts endocytosed were approximately ten percent of the total. The data from Table 1 indicate that the uptake of the $^3$H-cholesterylhexadecyl ether labeled liposomes is a first order reaction with respect to the liposomes and can be represented by the following equations.

($^3$H-cholesterylhexadecyl ether liposomes)$_{free}$ +
Platelets → ($^3$H-cholesterylhexadecyl ether liposomes)$_{endo}$ ·
d[endocytosed]/dt = k$_1$[free]
[free] approximately $7 \times 10^{11}$

[endocytosed] = k$_1$ [free] t

The slope of the line, [endocytosed] versus time equals k$_1$ [free]; therefore $k_1 = 7.1 \times 10^{-3} hr^{-1} M^{-1}$. It is noted that each platelet is capable of endocytosing an indeterminant amount of liposomes and the uptake of additional liposomes is not dependent on the amount previously endocytosed. Therefore the concentration of the platelet reaction sites is represented in the number k$_1$.

The release of the $^3$H-inulin probe after initial incubation of platelets with $^3$H-inulin labeled liposomes and subsequent washes follows first order reaction kinetics.

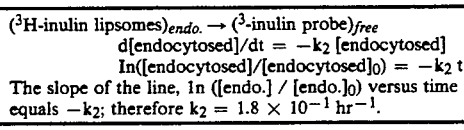

($^3$H-inulin lipsomes)$_{endo.}$ → ($^3$-inulin probe)$_{free}$
d[endocytosed]/dt = −k$_2$ [endocytosed]
ln([endocytosed]/[endocytosed]$_0$) = −k$_2$ t
The slope of the line, ln ([endo.] / [endo.]$_0$) versus time equals −k$_2$; therefore $k_2 = 1.8 \times 10^{-1} hr^{-1}$.

To verify the values of k$_1$ and K$_2$, we modeled the $^3$H-inulin liposomes uptake using the following kinetic scheme:

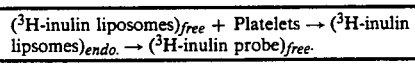

($^3$H-inulin liposomes)$_{free}$ + Platelets → ($^3$H-inulin lipsomes)$_{endo.}$ → ($^3$H-inulin probe)$_{free.}$ The equation, [endo.]/[lip. free]$_o$={k$_1$/(k$_2$−k$_1$)}{exp(−k$_1$t)−exp (−k$_2$t)}, provides a model for the experimental data for the 3H-inulin labeled liposome uptake that is in close agreement with the data (Table 11) and is consistent with our kinetic models.

TABLE 11

| Time, hours | 0.0 | 1.0 | 2.0 | 4.0 | 6.0 | 8.0 | 10.0 | 11.0 | 12.0 | 13.0 | 14.0 | 15.0 | 16.0 | 17.0 | 20.0 | 22.0 | 24.0 |
|---|---|---|---|---|---|---|---|---|---|---|---|---|---|---|---|---|---|
| #Lip. $\times 10^{10}$ (experimental) | 0.0 | 3.9 | 3.8 | 4.5 | 4.0 | 6.0 | — | 7.1 | — | 5.2 | — | 6.5 | 6.0 | 7.8 | 6.2 | 8.0 | 7.3 |
| #Lip. $\times 10^{10}$ (calculated) | 0.0 | 1.30 | 2.40 | 4.00 | 5.10 | 5.80 | 6.30 | — | 6.60 | — | 6.80 | — | 6.90 | — | 6.89 | 6.86 | 6.81 |

In Vitro Studies to Assess Platelet Function During Liposome Uptake

To determine if platelet characteristics are altered during liposome uptake, three physical parameters were measured in the presence or absence of liposomes. The parameters were: membrane integrity, extent of platelet aggregation and release of $^{14}$C-serotonin from granules. Each parameter was also determined in either Hans Balanced Salt Solution (HBSS) or Tyrodes buffer (Tyr) with 0.14 g/l CaCl$_2$ (Modified Tyrodes buffer).

Membrane integrity was determined using the fluorescein diacetate (FDA) assay. Briefly, after incubation of platelets suspended in HBSS or modified Tyrodes solution at 37° C., with or without liposomes, FDA was incubated (final concentration 4 μg/mL) with the platelets for 10 minutes at room temperature. The platelets were then kept on ice for 1 minute and pelleted. The fluorescence was measured at 520 nm emission while exciting at 489 nm.

FDA is a non-fluorescent probe which readily crosses the cell membrane. Within the cell the probe is hydrolysed by esterases to form fluorescent fluorescein which does not readily transverse the cell membrane but can leak out of the cells through membrane lesions. The leakage of fluorescein is a measure of loss of membrane integrity.

The results are shown in Table 12.

TABLE 12

| | Fluorescein Diacetate Assay | | | |
|---|---|---|---|---|
| Time | Tyr | Tyr + Lip | Hanks + Lip | Hanks |
| 0 | 1.00 | 1.00 | 1.00 | 1.00 |
| 1 | 0.779 | 0.807 | 0.736 | 0.752 |
| 3 | 0.471 | 0.557 | 0.713 | 0.599 |
| 5 | 0.279 | 0.250 | 0.345 | 0.380 |
| 7 | 0.209 | 0.200 | 0.046 | 0.102 |

Platelet aggregation was determined by suspending platelets in HBSS or modified Tyrodes solution followed by incubating at 37° C. in the presence or absence of liposomes. At various times the platelets were fixed with 1% glutaraldehyde and the percentage of aggregated platelets were determined by counting the cells in a hemacytometer. The counts are shown in Table 13.

TABLE 13

| | Microaggregation Assay | | | |
|---|---|---|---|---|
| Time | Tyr | Tyr + Lip | Hanks | Hanks + Lip |
| 0 | 6.5 | 0 | 1.2 | 0.4 |
| 1 | 1.1 | 1.8 | 16.8 | 9.1 |
| 3 | 5.9 | 1.1 | 30.6 | 22.3 |
| 5 | 2.7 | 3.2 | 36.4 | 20.2 |
| 7 | 2.3 | 7.7 | 46.0 | 33.2 |

The release of serotonin from platelets incubated in the presence or absence of liposomes was determined by incubating 1 μM $^{14}$C-serotonin with $3 \times 10^5$ platelets for 30 minutes at room temperature. Excess serotonin was removed by centrifugation; the platelets were resuspended in either HBSS or modified Tyrodes solution containing 2 μM in impramine to inhibit uptake of secreted serotonin. Following incubation at 37° C. for various times, with or without liposomes, ormaldehyde and EDTA, final concentrations of 0.006% and 50 μM, respectively, were added to halt further secretion. The platelets were pelleted and the percentages of radioactivity in the pellets were determined. The results are shown in Table 14.

TABLE 14

| | | Serotonin Release Assay | | | |
|---|---|---|---|---|---|
| Time Tyrodes | Time Hanks | Tyr | Tyr + Lip | Hanks | Hanks + Lip |
| 0 | 0 | 82.9 | 86.7 | 96.7 | 93.4 |
| 1 | 1 | 75.3 | 83.2 | 56.1 | 39.4 |
| 3 | 3 | 71.7 | 77.6 | 14.4 | 17.3 |
| 5 | 6 | 63.1 | 78.3 | 12.5 | 14.2 |
| 7 | — | 53.5 | 59.1 | — | — |

The above vitro assays demonstrate that although phagocytosis by platelets suspended in either HBSS or modified Tyrodes buffer is identical, the platelets do, however, spontaneously secrete serotonin, aggregate and lose membrane integrity more while suspended in HBSS. Regardless of the buffer, phagocytosis of liposomes does not significantly alter platelet secretion of serotonin or induce additional platelet aggregation or loss of membrane integrity.

EXAMPLE II

Characterization of Ligand-coupled Liposome Uptake of Platelets

Platelet uptake of liposomes having their surfaces covalently modified have also been characterized. The uptake mechanism was determined to proceed through receptor mediated endocytosis.

Liposomes were prepared as described in Example I and human gamma globulin (HgG) was covalently attached to their surfaces. The procedures for determining platelet uptake of these HgG-coupled liposomes were also described in Example I. HgG was isolated and coupled using procedures known to one skilled in the art. Briefly, liposomes were prepared by adding together 16 mg DSPC, 3.9 mg cholesterol and 0.94 mg MBPE (maleamidobutyryl phosphatidyl ethanolamine) and drying the mixture by evaporation. The dried lipids were desiccated for an additional 5–6 hours and then resuspended in 5 mls of PBS. The suspension was sonicated for 15 minutes to produce the liposomes. Heat aggregated human gamma globulin was prepared by heating a 30 to 50 percent solution of globulin in PBS at 62° C. for 30 minutes. The globulin (15 mg) was thiolated with 4 ul of a solution (2.7 mg/50 ul of DMF) of SATA(N-succinimidyl-S-acetylthioacetate; Calbiochem, La Jolla, Calif.). The mixture was vortexed and allowed to incubate at room temperature for 30 minutes. The resultant globulin with bound thioester groups was separated from free SATA by gel filtration on a Sephadex G-25 (Pharmacia, Piscataway, N.J.) column. The liposome coupling reaction was then carried out by the addition of 5 mg of the SATA-HgG with 5 ml of the sonicated MBPE-treated liposomes and the addition of 0.2 ml of 0.5 M hydroxylamine solution (pH 7.2). The mixture was incubated with gentle mixing at room temperature for 1 hour and the reaction stopped by the addition of 0.2 ml of N-ethylmaleimide (1 mg/ml in PBS). The free globulin was separated from the liposomes by gel filtration on a Biogel A 5m column (BioRad, Richmond, Calif.). Transferrin-coupled liposomes were generated using the same procedure.

HgG-coupled liposomes were taken up via specific cell surface interactions which involved the platelet Fc receptor. The uptake kinetics are shown in Table 15. Uptake of these liposomes resulted in the retention of both the lipid and aqueous components of the loading vehicle. The interaction was shown to be saturable since the preincubation of competitor liposomes or the addition of soluble HgG, which binds the Fc receptor, decreased HgG-coupled uptake. Additionally, uptake of HgG-coupled liposomes was not inhibited by the addition of dinitrophenol and iodoacetate, EDTA or cytochalasen B. These results indicate that HgG-coupled liposomes are taken up by platelets through a pathway similar or identical to receptor mediated endocytosis.

TABLE 15

Uptake vs Time for Control, HgG and $T_f$ Liposomes

| Time, hrs. | #Liposomes Per Platelet | | |
|---|---|---|---|
| | Control | $T_f$ | HgG |
| 1 | 45 | 480 | 1004 |
| 3 | 40 | 489 | 1382 |
| 5 | 63 | 552 | 1396 |
| 7 | 67 | 590 | 1355 |
| 8 | | 580 | |
| 9 | 67 | 462 | 1382 |
| 11 | 89 | 484 | 1326 |
| 13 | 123 | 711 | |
| 15 | 159 | 806 | |
| 17 | 206 | 819 | |
| 19 | 354 | 976 | |
| 12 | | | 1503 |
| 14 | | | 1390 |
| 16 | | | 1283 |
| 18 | | | 1508 |
| 20 | | | 1419 |
| 27 | | | 1673 |
| 23 | | | 1891 |

EXAMPLE III

Characterization of Reconstituted Sendai Virus Envelope (RSVE) Uptake by Platelets Platelet Uptake of $^{125}$I-labeled Sendai Virus This section shows the uptake of RSVE by platelets. Platelets were prepared as described in Example I. Sendai virus was prepared from ten day old chicken eggs which had been injected with 200 microliters of a 1/500 dilution of Z strain Sendai virus (approximately 1 mg/ml) in PBS (0.90% NaCl: 0.12% $Na_2HPO_4 \cdot 7H_2O$: 0.013% $NaH_2PO_4 \cdot H_2O$ w/w in water, pH 7.3) containing 1% penicillin and 1% streptomycin. Prior to injection the solution was filtered through an 800 nm Millipore filter. The inoculated eggs were incubated at 37° C. for three days. The eggs were then frozen at −20° C. for two hours to reduce bleeding during harvesting. The virus particles were harvested according to the protocols of Hoekstra et al., 1985, Supra and Maeda et al., Biochemistry 14:3736–3741, 1975, which is incorporated herein by reference.

For $^{125}$I-labeling of the virus, approximately $4 \times 10^{12}$ SV or reconstituted Sendai virus envelopes (RSVE) were mixed with 0.5 mCi of $Na^{125}I$ (Amersham, Corp.) in HBSS. Forty microliters of a 10 mg/ml solution of chloramine T was added and mixed gently for one minute. Subsequently two hundred microliters of a 4 mg/ml solution of sodium metabisulfite was added and mixed gently for five minutes. Both solutions were made immediately before use. The virus were centrifuged at 30,000 rpm (approximately 84,000 g) in an L 5-65 Beckman Ultracentrifuge using an SW50.1 rotor for forty minutes to remove excess $^{125}$I and resuspended in HBSS.

The virus particles and platelets were incubated in 1.5 mL polypropylene centrifuge tubes for the desired incubation times and temperatures, after which the mixtures were centrifuged at 5700 g for 5 minutes in a Beckman Microfuge 11. The pellets were washed twice in 0.9% saline solution and finally resuspended in 0.5 M NaOH/0.5% SDS and incubated overnight at room temperature. Solutions containing $^{125}$I were gamma counted with a Beckman Biogamma II; solutions containing $^3$H-inulin were mixed with 10 mL Safety Solve (Research Products, Inc.), allowed to sit at least two hours and scintillation counted with a Beckman LS 6000. For each experiment all samples were done in duplicate and all experiments were performed at least twice.

$^{125}$I-labeled virus particles were incubated with platelets for various incubation times, concentrations of the virus and incubation temperatures. The values reported for the uptake as determined by the use of $^{125}$I do not differentiate between binding, fusion and phagocytosis. Platelet uptake of the $^{125}$I-labeled virus particles increased with increasing incubation times over the 24 hour range, but after 15 to 20 hours showed signs of saturation, Table 16. After incubation of $3 \times 10^8$ platelets with $4.9 \times 10^{10}$ virus particles for 24 hours, approximately 45 virus particles were associated with each platelet. Viral uptake increased with increasing numbers of virus incubated and showed saturation at higher concentration values; two incubation times are given in Table 17. Incubation for 17.5 hours resulted in only slightly greater uptake values than the 12.5 hour incubation which suggests the onset of uptake saturation during these incubation times. Uptake at 37° C. was greater than uptake at 4° C.; at both temperatures uptake increased with increasing numbers of virus incubated until saturation, Table 18. When $9.9 \times 10^{10}$ virus particles were incubated with $3 \times 10^8$ platelets for 12 hours, the ratios of virus particles to platelets were 110 virus/platelet for 37° C. and 50 virus/platelet at 4° C.

TABLE 16

| Time, hours | 1.0 | 2.0 | 4.0 | 6.0 | 10.0 | 14.0 | 16.0 | 18.0 | 20.0 | 25.0 |
|---|---|---|---|---|---|---|---|---|---|---|
| #SV per Platelet | 23 | 27 | 33 | 34 | 39 | 41 | 43 | 44 | 48 | 42 |

TABLE 17

| #SV $\times 10^{10}$ Added | 1.2 | 2.5 | 4.9 | 9.9 | 19.8 | 39.5 |
|---|---|---|---|---|---|---|
| #SV per Platelet (17.5 hours) | 7 | 13 | 27 | 43 | 65 | 113 |
| #SV per Platelet (12.5 hours) | 4 | 12 | 24 | 41 | 60 | 100 |

TABLE 18

| #SV $\times 10^{10}$ Added | 1.2 | 2.4 | 4.9 | 9.9 | 19.8 |
|---|---|---|---|---|---|
| #SV per Platelet (37° C.) | 10 | 13 | 69 | 101 | 115 |
| #SV per Platelet (4° C.) | 9 | 14 | 23 | 51 | 68 |

Platelet Retention of Lipid and Aqueous Components of RSVE

This section shows that both the aqueous and membrane components of RSVE were retained following platelet uptake.

Incubations, RSVE preparation and $^{125}$I-labeling were performed as described above. $^3$H-inulin labeled reconstituted virus particles were prepared using a modified procedure of Loyter et al., Methods of Biochemical Analysis, Vol. 33, David Glick, editor. John Wiley and Sons, 1988, which is incorporated herein by reference. Three milligrams of SV were pelleted at 30 krpm (84,000 g) for 40 minutes at 4° C. The pellet was resuspended in 100 microliters of a solution A (100 mM NaCl, 50 μCi $^3$H-inulin (Amersham Corp.), 10% Triton X-100, 0.1 mM phenylmethyl sulfonyl fluoride (Sigma Chemical Co.) and 50 mM Tris HCl buffered to pH=7.4) and shaken for one hour at room temperature. The mixture was centrifuged under the same conditions as above; the supernatant was removed and shaken with 50 mg of SM-2 beads (Bio-Rad, Inc.) for 3-4 hours. An additional 50 mg of beads and 100 microliters of solution B (100 mM NaCl, 50 mM Tris HCl and 5 mM EDTA buffered to pH =7.4) was then added and shaken for 12-14 hours. Reconstituted virus envelopes were obtained by centrifuging at 30 krpm (84,000 g) for 40 minutes at 4° C. and resuspending the pellet in solution B.

To study the possible exocytosis of the reconstituted virus particles, the amounts of $^{125}$I and $^3$H-inulin released from platelets following uptake were examined. Briefly, platelets and $^{125}$I-labeled or $^3$H-inulin labeled reconstituted virus particles were incubated as above. The mixtures were centrifuged and the platelets washed by centrifugation twice in HBSS and further incubated at 37° C. for varying amounts of time. Both the pellets and supernatants were collected by centrifugation, solubilized in NaOH/SDS solution overnight. Solutions containing $^{125}$I were gamma counted; solutions containing $^3$H-inulin were allowed to sit at least two hours and scintillation counted. Table 19 documents that after 12 hours no membrane protein associated probe or aqueous phase probe were released.

TABLE 19

| Time, hours | 0.0 | 1.0 | 2.0 | 3.0 | 4.0 | 5.0 | 6.0 |
|---|---|---|---|---|---|---|---|
| $^3$H-label | 34 | 31 | 38 | 43 | 35 | 37 | — |
| $^{125}$I-label | 11 | 18 | — | 23 | — | 26 | 27 |

Saturability and Inhibition of Viral Uptake

This section shows that RSVE uptake by platelets is saturable. It also shows that compounds which inhibit fusion also inhibit platelet uptake of RSVE.

A competitive assay was performed to study the saturation of viral uptake. Preincubation of the platelets with non-radiolabeled virus particles prior to incubation with $^{125}$I-labeled virus particles for preincubation times of 0.5 and 6 hours and incubation times of 2 and 6 hours resulted in decreased uptake with increasing amounts of non-radiolabeled virus particles added. In addition, increased preincubation times resulted in less uptake of the labeled virus particles.

Fusion and platelet phagocytosis are two very different processes which can each be inhibited using different agents. Preincubation of virus particles with 50 μg/ml of either of the receptor gangliosides GD1a or GT1b at 37° C. decreased uptake; however, inhibition due to GT1b was slightly greater Table 20. Trypsinization using 40 μg/ml of trypsin followed by the addition of 80 μg/ml soybean trypsin inhibitor at 37° C. also inhibited fusion Table 21. Incubation in the presence of 1 mM EDTA, 4 μg/ml cytochalasin B or 2.5×10$^{-4}$M 2,4 dinitrophenol and 5×10$^{-5}$ M iodoacetate Table 22 did not inhibit fusion.

TABLE 20

| #SV × 10$^{10}$ Added | 1.2 | 2.5 | 4.9 | 9.9 | 19.8 |
|---|---|---|---|---|---|
| #SV per Platelet (Buffer) | 10 | 13 | 69 | 101 | 115 |
| #SV per Platelet (GT1b) | 6 | 9 | 16 | 24 | — |
| #SV per Platelet (GD1a) | 8 | 16 | 25 | 51 | 88 |

TABLE 21

| #SV × 10$^{10}$ Added | 1.3 | 2.4 | 4.9 | 9.9 | 19.0 |
|---|---|---|---|---|---|
| #SV per Platelet (Trypsin) | 3 | 5 | 9 | 18 | 42 |
| #SV per Platelet (Buffer) | 14 | 24 | 36 | 65 | — |

TABLE 22

| #SV × 10$^{10}$ Added | 1.3 | 2.4 | 4.9 | 9.9 | 19.0 |
|---|---|---|---|---|---|
| #SV per Platelet (Buffer) | 14 | 25 | 36 | 66 | — |
| #SV per Platelet (EDTA) | 13 | 20 | 37 | 68 | 117 |
| #SV per Platelet (Cytochalasin B) | 15 | 21 | 38 | 66 | 123 |
| #SV × 10$_{10}$ Added | 1.3 | 2.4 | 4.9 | 9.9 | 19.0 |
| #SV per Platelet (Buffer) | 7 | — | 18 | — | 55 |
| #SV per Platelet (dinitrophenol/Iodoacetate) | 6 | 10 | 17 | 28 | 52 |

HPTS Labeled RSVE Uptake

This section quantitates the percent of reconstituted virus particles phagocytosed and delivered to an acid compartment. In order to do this, the time dependence of the uptake of fluorescently labeled (HPTS) reconstituted virus particles was measured by fluorimetry.

HPTS, 1-hydropyrene-3,6,8-trisulfonic acid (Molecular Probes), is a pH-dependent fluorescent dye, Daleke et al., Biochim. Biophys. Acta. 1024:352–366, 1990, which is incorporated herein by reference, which exhibits two major fluorescent maxima (403 and 460 nm) which have a complimentary pH dependence in the range 5–9; the peak at 403 is maximal at low pH while the peak at 460 nm are relatively pH-dependent and can be used to standardize the concentration of dye associated with the cells. The fraction of dye taken up by endocytosis and delivered to an acidic compartment is calculated using the 460/413 nm ratio (or 460/447 nm ratio) and the equation: Ratio$_{pH\ 7.4}$—ratio$_{pH\ 6.0}$) Fraction endocytosed =(ratio$_{pH\ 7.4}$—ratio$_{measured}$)/ where ratio$_{measured}$ is the 460/413 ratio of the virus treated cells and ratio$_{pH\ 7.4}$ and ratio$_{pH\ 6.0}$ are the 460/413 ratios of virus in HBSS and acidified HBSS respectively. In the original paper by Daleke et al., Supra, the second peak occurred at 450 nm; however, according to our data the peak maximum is at 460 nm.

HPTS labeled RSVE were prepared according to the procedure for $^3$H-inulin labeled RSVE using a modification of solution A (75 mM NaCl, 35 mM HPTS, 10% Triton X-100, 0.1 mM PMSF and 50 mM Tris HCl buffered to pH=7.4). After incubation of HPTS labeled reconstituted virus envelopes for various times, the cells were washed twice with HBSS. Fluorescence excitation spectra (Lambda$_{ex}$ 395–465 nm, 4 nm bandwidth) were measured at 510 nm emission (4 nm bandwidth) using a SLM 4800 spectrofluorimeter (SLM Instruments, Inc.) with a stirred, temperature controlled cuvette (20° C.). The 447 nm fluorescence values were used to standardize the data. Degradation of the probe resulted in a peak at 432 nm which interfered with the readings at 413 nm.

The results showed no change in the pH-dependent fluorescence, indicating that RSVE did not accumulate in acid-containing vacuoles.

RSVE Fusion With Platelets

This section demonstrates fusion as a mechanism for RSVE uptake by platelets.

An $R_{18}$ fluorescent assay was employed to study fusion of Sendai virus particles with platelets. This assay allowed characterization of the temperature, pH, viral concentration and platelet concentration dependencies. The fluorescent probe Octadecylrhodamine B ($R_{18}$) has been used by a number of other workers to investigate viral fusion, for a general review see Loyter et al., supra. The probe inserts spontaneously into the viral membrane and rapidly equilibrates throughout the target membrane when fusion occurs. The probe self-dequenches by resonant energy transfer and subsequent trivial decay mechanisms due to the overlap of the emission and excitation fluorescence bands. In dilute concentrations (10% of the lipid content), the fluorescent dequenching is linearly proportional to the concentration of the probe in the membrane, Hoekstra et al., 1984, Supra. Upon fusion of the virus with a cell, the probe dilutes into the target membrane and dequenches.

Ten microliters of a 1 mM of $R_{18}$ (Molecular Probe, Inc.) in ethanol was added to a one milliliter solution containing approximately two milligrams of SV (1 mg of protein=$1.3 \times 10^{12}$ SV) and incubated for one hour at room temperature. Excess $R_{18}$ was removed by centrifugation at 30 krpm (84,000g) for 40 minutes at 4° C. The pellet was resuspended in HBSS.

Fluorescent measurements were made in the SLM 4800 fluorimeter with a stirred, temperature controlled cuvette by monitoring the emission at 590 nm with an excitation wavelength of 560 nm. The temperature and pH dependencies of fusion were determined by performing kinetic experiments of thirty minute duration. $R_{18}$ labeled Sendai virus were preincubated at 37° C. in the cuvette with 2 ml of HBSS. Data collection was initiated and after a baseline had been established the platelets were added. At the conclusion of the experiments 1% Triton X-100 was added to determine the maximum fluorescent signal.

To determine the viral and platelet concentration dependencies of fusion, $R_{18}$ labeled Sendai virus particles were incubated with platelets at 37° C. for thirty minutes. Prior to and after incubation, fluorescence measurements were performed. One percent Triton X-100 was added to the samples at the conclusion of each experiment to determine the maximum fluorescent signal. Plots of the fluorescence versus time showed biphasic behavior for the fusion of virus particles with platelets. Initially the fluorescence increased rapidly for approximately two minutes and then continued at a slower rate of change until saturation. Fusion was maximal at 37° C. and pH=7.4 (Table 23). In addition, the percent fusion decreased with increasing numbers of virus particles added. Incubation of 150 mg of platelets (1 mg of protein=$3 \times 10^8$ platelets with 5 to 30 mg of virus (1 mg of protein=$1.3 \times 10^{12}$ Sendai virus particles; Hoekstra et al., 1984, Supra. at 37° C. for 30 minutes resulted in a decrease in the percent fusion, fused virus/total virus, from 10% to 4% while the percent fusion remained constant at approximately 4% at 4° C. over the same range. The percent fusion increased from 4% to 12% when 5 mg of virus were incubated with 50 to 200 mg of platelets for 30 minutes at 37° C. and decreased from 6% to 2% at 4° C. (Table 24). Reciprocal plots, platelets/fused virus versus platelets/virus added, of the data from (Table 24) were used to calculate the saturation of fusion sites on the platelet surface. Approximately 55 virus particles are capable of fusing with a platelet at 37° C.

TABLE 23

| pH | 4.0 | 5.0 | 6.0 | 7.0 | 7.5 | 8.0 | 9.0 | 10.0 | |
|---|---|---|---|---|---|---|---|---|---|
| % Fusion | 6.5 | 7.3 | 7.0 | 10.8 | 13.5 | 12.0 | 8.0 | 7.7 | |
| Temperature, °C. | 10 | 15 | 23 | 25 | 30 | 34 | 37 | 40 | 50 |
| % Fusion | 5 | 7 | 10 | 12 | 13 | 17 | 20 | 17 | 9 |

TABLE 24

| Micrograms of Virus | 5 | 10 | 15 | 20 | 25 | 30 |
|---|---|---|---|---|---|---|
| % Fusion, 37° C. | 8 | 6 | 4 | 5 | 2 | 3 |
| % Fusion, 4° C. | 3 | 3 | 4 | 3 | 4 | 3 |
| Micrograms of Platelets | 50 | 75 | 100 | 150 | 175 | 200 |
| % Fusion, 37° C. | 3 | 9 | 11 | 12 | 12 | 11 |
| % Fusion, 4° C. | 5 | 4 | 3 | 2 | 1 | 2 |

Uptake of $^{125}$I-labeled RSVE

This section quantitates the uptake of RSVE by platelets.

$^{125}$I-labeled reconstituted virus particles were incubated with platelets as described in Example IX using increasing numbers of RSVE. Assuming that the HN and F proteins are 25% of the total protein, Loyter A. and Volsky D. J., 1982, Supra, 1 μg of protein should correspond to 5.2 $\times 10^9$ virus. Using this conversion factor, more RSVE than virus were taken up by the platelets (Table 25). Incubation of $3 \times 10^8$ platelets with either $9.9 \times 10^{10}$ virus particles or $9.9 \times 10^{10}$ reconstituted virus particles at 37° C. for 12 hours, resulted in approximately 125 RSVE per platelet and 75 virus particles per platelet.

TABLE 25

| #RSVE (SV) $\times 10^{10}$ Added | 1.2 | 5.0 | 9.9 | 19.8 | 39.5 |
|---|---|---|---|---|---|
| #RSVE per Platelet | — | 62 | 119 | 221 | 298 |
| #SV per Platelet | 16 | 29 | 71 | 78 | — |

Localization of Virus Particles During Uptake

Electron microscopy was performed to investigate the location of the virus particles with respect to the platelets. A large number of virus particles were located within the OCS. In addition, many virus particles appeared to be bound to the outer cell surface. However, electron microscopy could not give conclusive evidence in determining whether fusion or platelet phagocytosis was occurring. Identification of the virus particles within the acid-containing vacuoles was not possible due to the vacuoles' high electron density. In addition, visualization of virus particles fusing with the cell membrane or the emptying of the viral contents into the cell was not possible.

EXAMPLE IV

In Vivo Targeting of Loaded Platelets

This example shows the targeting of loaded platelets to platelet localizing areas.

Platelets to be loaded were isolated from Sprague-Dawley rats. Briefly, five rats were sacrificed and their blood pooled into a syringe containing acid citrate dextrose (acd). The platelets were harvested by low-speed centrifugation.

Liposomes were used as the loading vehicles. Platelets were incubated at 37° C. for 0.5 hours in the presence or absence of liposomes following the conditions set forth in Example I. The platelets were labeled with indium oxine for easy detection of targeted areas.

Loaded platelets were administered to a rat by intravenous injection. As a control, the platelets incubated in the absence of liposomes were also administered to a separate rat. 25 minutes following injection, the rats were sacrificed and the amount of radioactivity in the spleen, liver and blood was determined using a gamma counter. The results are given in Table 26 and demonstrate the targeting of loaded platelets to platelet localizing areas. Moreover, the results also show that circulation is as efficient for loaded platelets as with unloaded platelets.

TABLE 26

| | In Vivo Targeting | | | |
|---|---|---|---|---|
| | | CPM | | |
| Animal | Platelets | Spleen | Liver | Blood (per ml) |
| 1 | loaded | 50,019 | 292,562 | 98,180 |
| 2 | unloaded | 66,365 | 671,349 | 73,805 |

Although the invention has been described with reference to the presently-preferred embodiments, it should be understood that various modifications can be made without departing from the spirit of the invention. Accordingly, the invention is limited only by the following claims.

We claim:

1. A composition consisting essentially of loaded blood platelets wherein said loaded blood platelets comprise:
   a blood platelet comprising a membrane and a cell interior surrounded by said membrane;
   a loading vehicle located within said blood platelet cell interior, said loading vehicle being selected from the group consisting of liposomes and reconstituted Sendai virus envelopes wherein said liposomes or reconstituted Sendai virus envelopes are of a size capable of being incorporated into the interior of said blood platelet; and
   a diagnostic or therapeutic agent encapsulated within said loading vehicle.

2. A composition according to claim 1 wherein said loading vehicle is a liposome selected from the group consisting of neutral unilamellar and multilamellar liposomes.

3. A composition according to claim 1 wherein said diagnostic or therapeutic agent is a macromolecule labeled with a radioisotope.

4. A composition according to claim 3 wherein said radioisotope is selected from the group consisting of gamma-emitters, positron-emitters and x-ray-emitters.

5. A composition according to claim 1 wherein said diagnostic or therapeutic agent is a therapeutic agent selected from the group consisting of Murimyl dipeptide, adriamycin, cis-platinum, interleukins and cytokines.

6. A composition comprising loaded blood platelets wherein said loaded blood platelets are prepared by a method comprising the steps of:
   providing blood platelets comprising a membrane and a cell interior surrounded by said membrane;
   providing loading vehicles wherein said loading vehicles are selected from the group consisting of liposomes and reconstituted Sendai virus envelopes wherein said liposomes or reconstituted Sendai virus envelopes are of a size capable of being incorporated into the interior of said blood platelet, and wherein said loading vehicles further comprise a diagnostic or therapeutic agent encapsulated therein; and
   combining said blood platelets with said loading vehicles to permit uptake of said loading vehicles into said blood platelet cell interior to form said loaded blood platelets.

7. A composition made by the method of claim 6 wherein said loading vehicle is a liposome selected from the group consisting of neutral unilamellar and multilamellar liposomes.

8. A composition made by the method of claim 6 wherein said diagnostic or therapeutic agent is a macromolecule labeled with a radioisotope.

9. A composition made by the method of claim 8 wherein said radioisotope is selected from the group consisting of gamma-emitters, positron-emitters and x-ray-emitters.

10. A composition made by the method of claim 6 wherein said diagnostic or therapeutic agent is a therapeutic agent selected from the group consisting of Murimyl dipeptide, adriamycin, cisplatinum, interleukins and cytokines.

* * * * *